US012788526B2

(12) United States Patent
Patel

(10) Patent No.: US 12,788,526 B2
(45) Date of Patent: *Nov. 10, 2026

(54) DURA SHIELD

(71) Applicant: SurGenTec, LLC, Boca Raton, FL (US)

(72) Inventor: Ashish Patel, Chicago, IL (US)

(73) Assignee: SurGenTec, LLC, Boca Raton, FL (US)

( * ) Notice: Subject to any disclaimer, the term of this patent is extended or adjusted under 35 U.S.C. 154(b) by 80 days.

This patent is subject to a terminal disclaimer.

(21) Appl. No.: 18/779,511

(22) Filed: Jul. 22, 2024

(65) Prior Publication Data

US 2025/0017682 A1 Jan. 16, 2025

Related U.S. Application Data

(63) Continuation of application No. 17/201,657, filed on Mar. 15, 2021, now Pat. No. 12,042,337.

(60) Provisional application No. 63/042,175, filed on Jun. 22, 2020, provisional application No. 62/989,383, filed on Mar. 13, 2020.

(51) Int. Cl.

| | |
|---|---|
| ***A61B 90/00*** | (2016.01) |
| ***A61B 17/00*** | (2006.01) |
| ***A61B 17/02*** | (2006.01) |
| ***A61L 31/10*** | (2006.01) |
| ***A61L 31/16*** | (2006.01) |

(52) U.S. Cl.

CPC .............. *A61B 90/08* (2016.02); *A61B 90/03* (2016.02); *A61L 31/10* (2013.01); *A61L 31/16* (2013.01); *A61B 2017/00367* (2013.01); *A61B 2017/00889* (2013.01); *A61B 2017/0212* (2013.01); *A61B 17/0218* (2013.01); *A61B 2017/0262* (2013.01); *A61B 2090/036* (2016.02); *A61B 2090/08021* (2016.02); *A61L 2300/402* (2013.01); *A61L 2300/404* (2013.01)

(58) Field of Classification Search

CPC ...... A61B 17/0218; A61B 2017/00367; A61B 2017/00889; A61B 2017/0212; A61B 2090/08021; A61B 2017/0262; A61B 2090/036; A61B 17/7053; A61B 17/02; A61B 2017/0225; A61B 17/025; A61B 2017/0256; A61F 2/30767

See application file for complete search history.

(56) References Cited

U.S. PATENT DOCUMENTS

| | | | | |
|---|---|---|---|---|
| 9,526,533 | B1 * | 12/2016 | Aranibar ............ | A61B 17/7058 |
| 10,694,934 | B2 | 6/2020 | Wales et al. | |
| 12,042,337 | B2 | 7/2024 | Patel | |
| 2003/0078588 | A1 | 4/2003 | Alleyne | |

(Continued)

*Primary Examiner* — Eduardo C Robert
*Assistant Examiner* — Tara Rose E Carter
(74) *Attorney, Agent, or Firm* — Knobbe Martens Olson & Bear, LLP

(57) ABSTRACT

Dura shields in accordance with embodiments of the invention are disclosed. In one embodiment, a dura shield includes a shield configured to protect a patient's dura during an interbody procedure, a tether coupled to the shield and configured to position the shield, and an anchor coupled to the shield and configured to attach to a surface within the patient during the interbody procedure. A variety of sensors can be incorporated into the dura shield in order to monitor a patient during the procedure.

20 Claims, 7 Drawing Sheets

(56) References Cited

U.S. PATENT DOCUMENTS

| | | | | |
|---|---|---|---|---|
| 2005/0126576 | A1 * | 6/2005 | Ferree ........................ | A61F 2/00 128/846 |
| 2007/0055111 | A1 * | 3/2007 | Morgan ............. | A61B 17/7074 600/235 |
| 2010/0094425 | A1 | 4/2010 | Bentley | |
| 2011/0054260 | A1 * | 3/2011 | Albrecht ............ | A61B 17/3496 600/208 |
| 2011/0172682 | A1 | 7/2011 | Brady | |
| 2012/0095296 | A1 | 4/2012 | Trieu et al. | |
| 2012/0283520 | A1 | 11/2012 | Kleyman | |
| 2012/0283835 | A1 | 11/2012 | Bentley | |
| 2015/0343205 | A1 | 12/2015 | Howard et al. | |
| 2016/0067494 | A1 | 3/2016 | Lipani | |
| 2016/0135834 | A1 | 5/2016 | Bleich et al. | |
| 2016/0206348 | A1 | 7/2016 | Wilson | |
| 2017/0065269 | A1 | 3/2017 | Thommen et al. | |
| 2017/0367731 | A1 | 12/2017 | Mark et al. | |
| 2019/0117254 | A1 | 4/2019 | Mark et al. | |
| 2025/0331887 | A1 | 10/2025 | Patel | |

* cited by examiner

DURA SHIELD

CROSS-REFERENCE TO RELATED APPLICATIONS

The application is a continuation of U.S. Non-Provisional patent application Ser. No. 17/201,657 filed on Mar. 15, 2021, which claims priority to U.S. Provisional Patent Application No. 62/989,383, titled "Dura Shield" and filed Mar. 13, 2020, and to U.S. Provisional Patent Application No. 63/042,175, titled "Dura Shield with Integrated Sensor Devices" and filed Jun. 22, 2020, the disclosures of which are hereby incorporated by reference in their entirety.

TECHNICAL FIELD

The present invention is generally related to medical devices and more specifically retractors used during surgery.

BACKGROUND

Dura is a membrane that surrounds the brain and spinal cord, protecting the central nervous system. The dura has several layers containing cerebrospinal fluid and nerves.

SUMMARY

Dura shields in accordance with embodiments of the invention are disclosed.

In one embodiment, a dura shield includes a shield configured to protect a patient's dura during an interbody procedure, a tether coupled to the shield and configured to position the shield, and an anchor coupled to the shield and configured to attach to a surface within the patient during the interbody procedure.

In yet another embodiment of the invention, the shield is constructed using a material selected from the group consisting of plastic, rubber, sponge, neoprene, polyethylene fibers, and Kevlar.

In still another embodiment of the invention, the shield comprises a first layer constructed using a first material selected from the group and a second layer constructed using a second material selected from the group, the first material differing from the second material.

In yet still another embodiment of the invention, the first layer provides an abrasion-resistant surface.

In yet another additional embodiment of the invention, the second layer provides a padded surface.

In still another additional embodiment of the invention, the tether is located between the first layer and the second layer.

In yet still another additional embodiment of the invention, the shield comprises an antibacterial treatment.

In yet another embodiment of the invention, the shield comprises a soothing treatment.

In still another embodiment of the invention, the surface is selected from the group consisting of an annulus of a spinal disc, a spinal disc, and a bone.

In yet still another embodiment of the invention, the anchor is selected from the group consisting of a staple, a hook, a screw, and an adhesive.

In yet another additional embodiment of the invention, the tether is constructed from a material selected from the group consisting of a plastic, a rubber, and a metal.

In still another additional embodiment of the invention, the dura shield comprises an unopened state where the shield is rolled around the tether and an opened state where the shield is unrolled and the tether can be used to adjust the positioning of the shield.

In yet still another additional embodiment of the invention, the anchor is attached to the surface when the dura shield is in the opened state.

In yet another embodiment of the invention, the dura shield includes an applicator configured to hold the dura shield when the dura shield is in the unopened state.

In still another embodiment of the invention, the applicator is configured to transition the dura shield from the unopened state to the opened state by unrolling the shield from around the tether as the applicator is withdrawn from the surface.

Yet another embodiment of the invention includes a method for attaching a dura shield including inserting, into a piston of an applicator, a dura shield in an unopened state, wherein an anchor of the dura shield extends beyond a first end of the piston, placing the anchor on a surface, actuating a trigger of the applicator to cause the piston to move toward an applicator tip of the applicator and to attach to the surface, and deploying the dura shield by withdrawing the piston from the applicator tip, wherein withdrawing the piston causes the dura shield to move from the unopened state to an opened state.

In yet another embodiment of the invention, the method further includes manipulating a location of the dura shield by moving a tether of the dura shield using the applicator.

In still another embodiment of the invention, causing the anchor to attach to the surface comprises compressing a staple.

In yet still another additional embodiment of the invention, causing the anchor to attach to the surface comprises turning a screw.

Still another embodiment of the invention includes a dura shield including a tether, a shield configured to protect a patient's dura during an interbody procedure and coupled to the tether, the shield comprising a rolled state where the shield is rolled around a tether and an unrolled state wherein the shield is unrolled and the tether can be used to adjust positioning of the shield, a staple coupled to the shield and configured to attach to an annulus of a spinal disc within the patient during the interbody procedure, and an applicator configured to hold the dura shield when the shield is in the rolled state and configured to manipulate the shield from the rolled state to the unrolled state Other objects, advantages and novel features, and further scope of applicability of the present invention can be set forth in part in the detailed description to follow, and in part can become apparent to those skilled in the art upon examination of the following, or can be learned by practice of the invention. The objects and advantages of the invention can be realized and attained by means of the instrumentalities and combinations particularly pointed out in the claims.

BRIEF DESCRIPTION OF THE DRAWINGS

The description can be more fully understood with reference to the following figures, which are presented as exemplary embodiments of the invention and should not be construed as a complete recitation of the scope of the invention, wherein.

DETAILED DESCRIPTION

Figure 1:
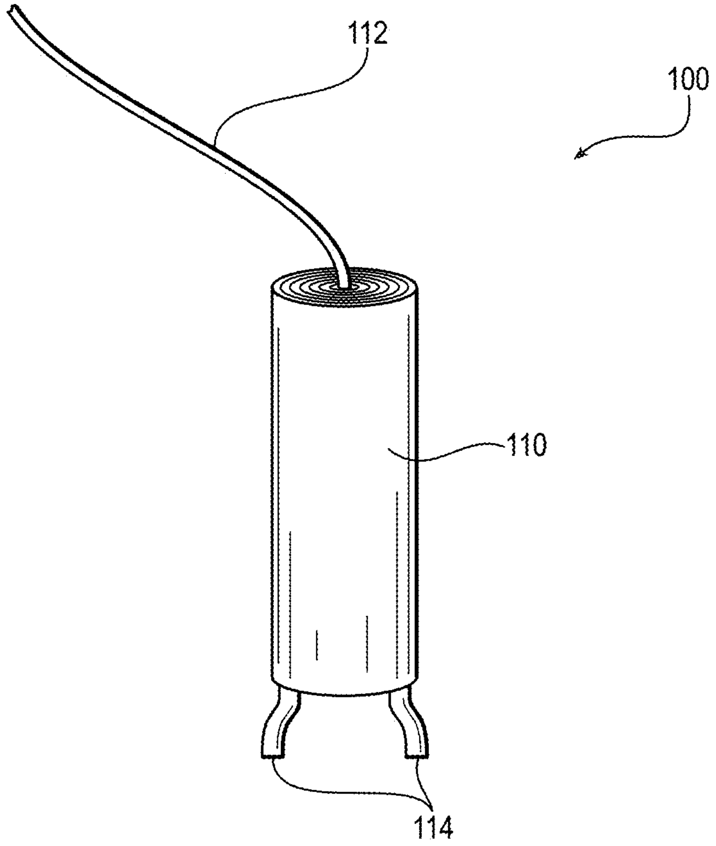
FIG. 1 is a line drawing of an unopened dura shield in accordance with an embodiment of the invention.

Turning now to the drawings, dura shields in accordance with embodiments of the invention are disclosed. Interbody cages are typically titanium structures surgically inserted in the spinal disc space. The interbody cage is usually porous and permit bone grafts to grow from the vertebral body through the cage and into the next vertebral body. During surgery, such as spinal surgeries, several elements are under risk for injury including, but not limited to, nerves and blood vessels. While the following is described with respect to spinal surgeries, dura shields can also be used for several applications occurring during a wide variety of medical procedures.

Interbody fusion surgeries, such as lumbar fusions, creates connections between adjoining vertebra, thereby eliminating any movement between the bones. A variety of lumbar fusion surgeries are commonly utilized, such as transforaminal lumbar interbody fusion (TLIF), posterior lumbar interbody fusion (PLIF), anterior lumbar interbody fusion (ALIF), lateral interbody fusion (LLIF), and the like. TLIF fuses the anterior (front) and posterior (back) columns of the spine, where the anterior portion of the spine is stabilized by the bone graft and interbody spacer and the posterior column is locked in place with pedicle screws, rods, and/or bone graft. PLIF includes approaching the spine through the back and inserting a cage made of either allograft bone or synthetic material (e.g. titanium) directly into the disc space of the spine. ALIF and LLIF are similar to PLIF in that these procedures include inserting a cage made of either allograft bone or synthetic material (e.g. titanium) directly into the disc space of the spine; however, in ALIF the spine is approached through the peritoneum while in LLIF a retroperitoneal approach to the spine is utilized.

When an interbody fusion is performed, the dura (which includes the lumbar nerve roots) is mobilized and retracted medially. The exiting nerve root at times is retracted superiorly or laterally as needed. This then uncovers the spinal disc space that will be accessed for interbody fusion. The dura is typically retracted with a metallic nerve root retractor held for the duration of the interbody fusion, usually by an assistant. Not only does this typically leave the assistant unable to perform other duties, the retraction of the dura can lead to a variety of problems, such as the dura being impacted and/or damaged during the surgical procedure. This can lead to nerve damage and/or the leaking of spinal fluid occurring during surgery, requiring additional procedures to correct, potential complications from the surgery, and additional recovery time for the patient.

Dura shields disclosed herein are designed to replace the metallic dura retractor typically used during interbody fusion surgeries. A dura shield provides a barrier between instruments working in the spinal disc space and the dura which is at risk for injury and to define the working corridor during these procedures. The dura shield can be anchored so that it protects the dura from impacts and/or abrasion. The dura shield can be anchored to the annulus of the spinal disc through a staple or other attachment device. In the event of minimal annulus, the dura shield can also be anchored to the bone inside the disc space. The dura shield can include a tether that can be used to position the dura shield and/or hold the dura in place. In this way, the dura shield disclosed herein can replace both the dura retractor and the assistant during the operation while adding additional safeguards to the dura, reducing complications, and reducing recovery time. This ‘dura retraction’ can be automated with the dura shield versus the standard practices typically employed.

In a variety of embodiments, the dura shield includes one or more sensors and/or sensing surfaces. These sensors and/or sensing surfaces can be detected by a variety of devices, such as surgical robots and spinal navigation devices, while the device is performing one or more actions during the operation. The device can use the sensors and/or sensing surfaces to identify the range in which the device can move and/or perform actions during the operation.

Turning now to FIG. 1, a line drawing of an unopened dura shield in accordance with an embodiment of the invention is shown. Internal portions of the device are shown in dotted lines. The dura shield 100 includes a shield 110, a tether 112, and an anchor 114. In the unopened state, the shield 110 is wrapped around the tether 112 and/or anchor 114. The shield 110 can be made of any material, such as plastic, rubber, sponge, neoprene, polyethylene fibers, Kevlar, and/or any other material that provides padding and/or abrasion resistance as appropriate. In several embodiments, the shield 110 is made from a single material. In a variety of embodiments, the shield 110 includes two or more layers. In many embodiments, one or more of the layers of the shield 110 are made from different materials. For example, the shield 110 can include a top layer made from an abrasion-resistant material and a bottom layer that is made from a padded material. In a number of embodiments, the shield 110 utilizes multiple materials in a single layer. For example, the shield can have a lower portion made from rubber and an upper portion made from a padded material, such as a sponge and/or neoprene.

The tether 112 can be used to position the shield 110 once deployed and/or hold back a portion of the body, such as the dura. In several embodiments, the tether 112 is attached to the shield 110 and/or anchor 114. The tether 112 can be constructed out of any material, such as plastic, rubber, and/or metal, as appropriate. The tether 112 may be affixed to an external surface and/or weighted to cause the shield 110 to stay in contact with a desired surface once deployed.

The anchor 114 can be used to couple the shield 110 and/or tether 112 to one or more bodies or surfaces within a surgical space. For example, during a spinal surgery, the anchor 114 can be attached to an annulus of a spinal disc. However, the anchor 114 can attach to any surface, such as directly to the bone of the spinal disc, as appropriate. The anchor 114 can include, but is not limited to, a staple, a hook, a screw, an adhesive, and the like. The anchor 114 can be constructed out of any material that is suitable for interaction with the corresponding attachment surface. For example, the anchor 114 can be constructed using a ductile material that allows for the anchor 114 to wrap around an annulus of a spinal disc. In another example, the anchor 114 can be a staple constructed using a metal that is formulated to allow penetration into bone without being so hard that it causes the bone to break. In several embodiments, the anchor 114 is constructed using a plastic. In many embodiments, a first end of the anchor 144 is coated in an adhesive that couples the anchor 114 to a bone and/or any other surface in a body. The adhesive can be any non-permanent adhesive as appropriate. In a variety of embodiments, the adhesive is temperature-dependent such that the adhesive adheres to a surface, such as a disc or bone, at typical body temperatures and releases at a temperature above normal body temperature. Any temperature differential, such as 10 degrees, between the temperature at which the adhesive will couple the anchor 114 to the surface and the temperature at which the adhesive will release the anchor 114 from the surface can be used as appropriate.

A variety of treatments and/or coatings can be applied to the shield 110, tether 112, and/or anchor 114 as appropriate. For example, antibacterial and/or soothing compounds can be applied to the shield 110. These compounds can be used to treat the shield 110 to reduce the risk of infections and complications from contaminants during surgery.

Figure 2A:
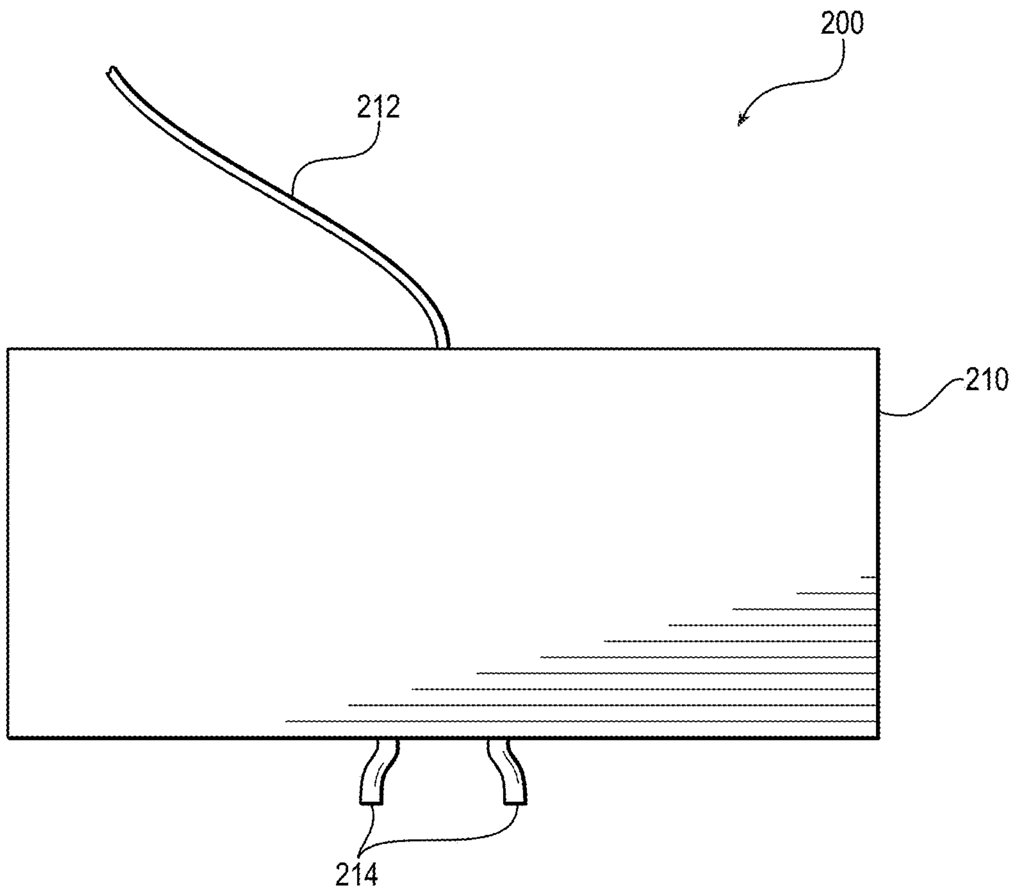
FIG. 2A is a line drawing of an opened dura shield in accordance with an embodiment of the invention.

Turning now to FIG. 2A, a line drawing of an opened dura shield in accordance with an embodiment of the invention is shown. Internal portions of the device are shown in dotted lines. The dura shield 200 includes a shield 210, a tether 212, and an anchor 214. In the opened state, the shield 210 is unrolled and lies substantially in contact with a surface. For example, the shield 210 can be substantially in contact with the retracted dura after the dura has been opened during an interbody surgery. The shield 210 may be oriented in any orientation relative to the spine depending on the specific incisions made to open and retract the dura from the spinal disc(s) being targeted during the surgery. This can be placed for a cervical, thoracic, and/or lumbar procedure to retract and protect structures that may be injured during the interbody work. This includes the dura and nerve root(s) during TLIF procedure, the big blood vessels during ALIF procedure of the anterior longitudinal ligament, and/or lumbar plexus nerves during the LLIF procedure of the lung during procedures in the thoracic spine.

The dura shield can be packaged such that is automatically deploys from an unopened state to an opened state once the anchor 214 is affixed to a body and the dura shield 200 is removed from an applicator. In a variety of embodiments, the shield 210 is manually unrolled onto the surface. Once unrolled, the tether 212 can be used to maintain the shield 210 in contact with the surface. In several embodiments, the tether 212 maintains the shield 210 in movable contact with the surface such that the tether 212 can be used to adjust the positioning of the shield 210 with respect to the surface.

Figure 2B:
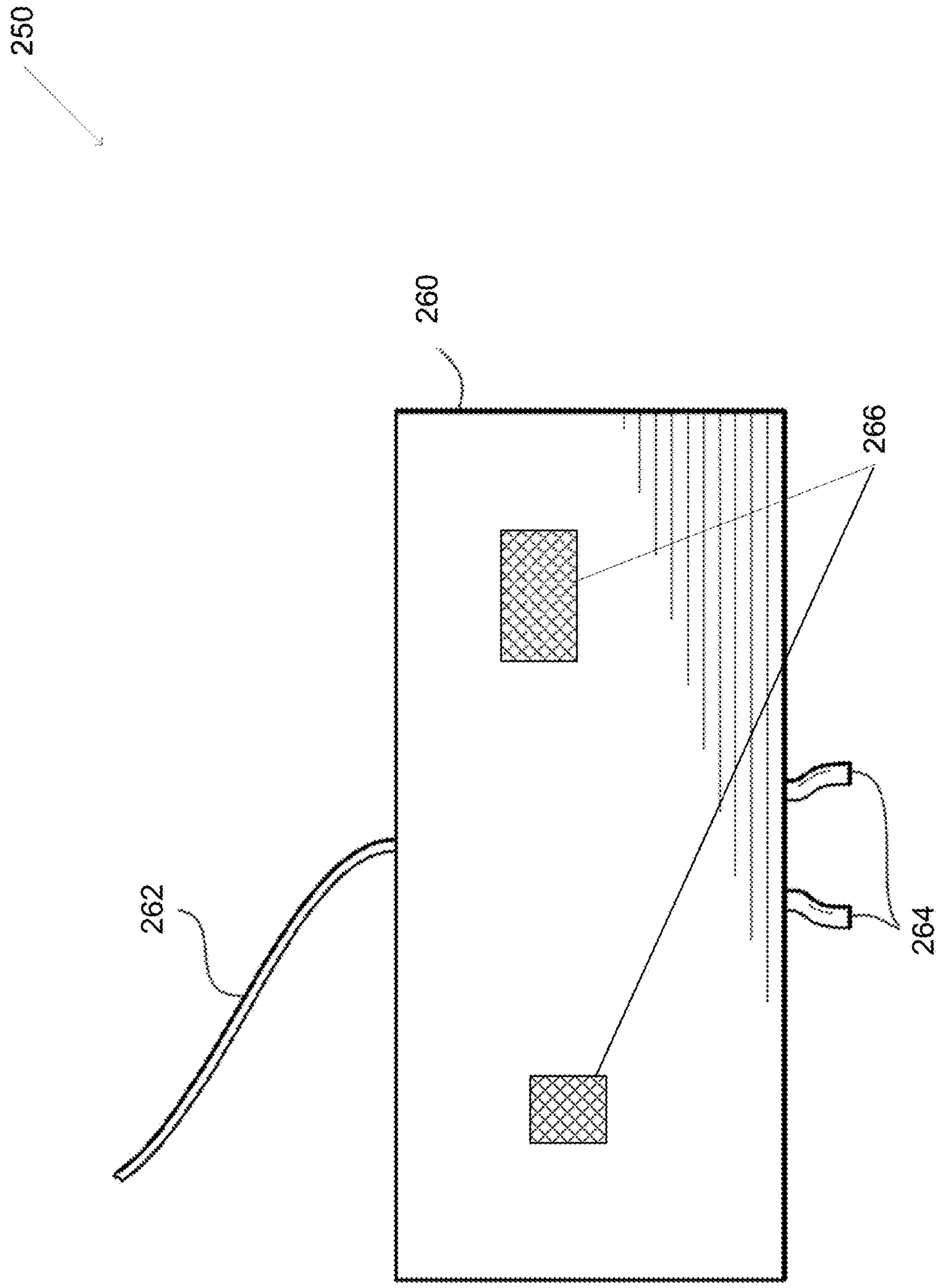
FIG. 2B is a line drawing of an opened dura shield in accordance with an embodiment of the invention.

Turning now to FIG. 2B, a line drawing of an opened dura shield with sensor devices in accordance with an embodiment of the invention is shown. The dura shield 250 includes a shield 260, a tether 262, an anchor 264, and one or more sensor devices 266. In the opened state, the shield 260 is unrolled and lies substantially in contact with a surface. For example, the shield 260 can be substantially in contact with the retracted dura after the dura has been opened during a spinal surgery. The shield 260 may be oriented in any orientation relative to the spine depending on the specific incisions made to open and retract the dura from the spinal disc(s) being targeted during the surgery. The dura shield can be packaged such that is automatically deploys from an unopened state to an opened state once the anchor 264 is affixed to an attachment surface and the dura shield 250 is removed from an applicator. In a variety of embodiments, the shield 260 is manually unrolled onto the surface. Once unrolled, the tether 262 can be used to maintain the shield 260 in contact with the surface. In several embodiments, the tether 262 maintains the shield 260 in movable contact with the surface such that the tether 262 can be used to adjust the positioning of the shield 260 with respect to the surface.

The one or more sensor devices 264 can be located in a variety of locations within dura shield 250. As shown, the dura shield 250 includes two sensor devices located on a first end and a second end of shield 260. However, any number of sensors devices can be located in dura shield 250, and the sensor devices can be located within shield 260, tether 262, and/or anchor 264 as appropriate. In many embodiments, the sensor devices 264 cover the entire surface (or, when the shield 260 includes multiple layers, an entire layer) of the shield 260.

The sensor devices 264 can provide an indication regarding the location of the dura shield 250 to a variety of surgical devices, such as robotic surgical devices and spinal navigation devices. As the dura shield 250 is located adjacent to sensitive structures within an operating environment, such as nerves and blood vessels, the sensor devices 264 can provide the devices with an indication of the contours of the effective borders of the surgical area within the operating environment. In this way, the sensor devices 264 can provide feedback to the surgical devices such that the devices can limit their range of motion to an area within the region protected by the dura shield 250.

The sensor devices 264 can be made from a variety of materials. In many embodiments, the sensor devices 264 include a colored and/or reflective surface on the top of shield 260 that can be detected using a variety of sensors, such as light sensors and/or color sensors. For example, the surface of shield 260 can be colored bright green (or any other color that does not naturally occur within the operating environment) that can be detected by a sensor in a surgical device. In a number of embodiments, the color and/or reflectivity of the shield 260 is such that it can be detected even if the surface of shield 260 is covered in material deposited on shield 260 during a surgical procedure. In several embodiments, sensor devices 264 include low-power radio devices, such as a Bluetooth low energy devices, radio frequency identification (RFID) tags, and/or near field communication (NFC) tags. These low-power radio devices can include a microprocessor and/or an antenna that is powered by an interrogator located in the surgical device. When activated, the sensor devices 264 can indicate that the surgical device is located within a threshold distance of the dura shield 250. In a number of embodiments, the sensor devices 264 include temperature and/or blood flow sensors (or any other sensors) that can monitor conditions of the patient during the surgical procedure. In a variety of embodiments, the dura shield 250 includes an energy harvester, such as a harvester that converts heat to electricity, to power the sensor devices 264. The sensor devices 264 can transmit the sensor data to the surgical devices when the surgical device is within trans-mission range of the sensor devices 264. The dura shield 250 can also include energy storage devices, such as capacitors, to store energy generated by the energy harvester and/or to power the sensor devices 264.

Although a variety of dura shields are shown and described with respect to FIGS. 2A-B, any of a variety of constructions, including those that utilize sensors located externally to the shield, can be utilized in accordance with embodiments of the invention.

Figure 3A:
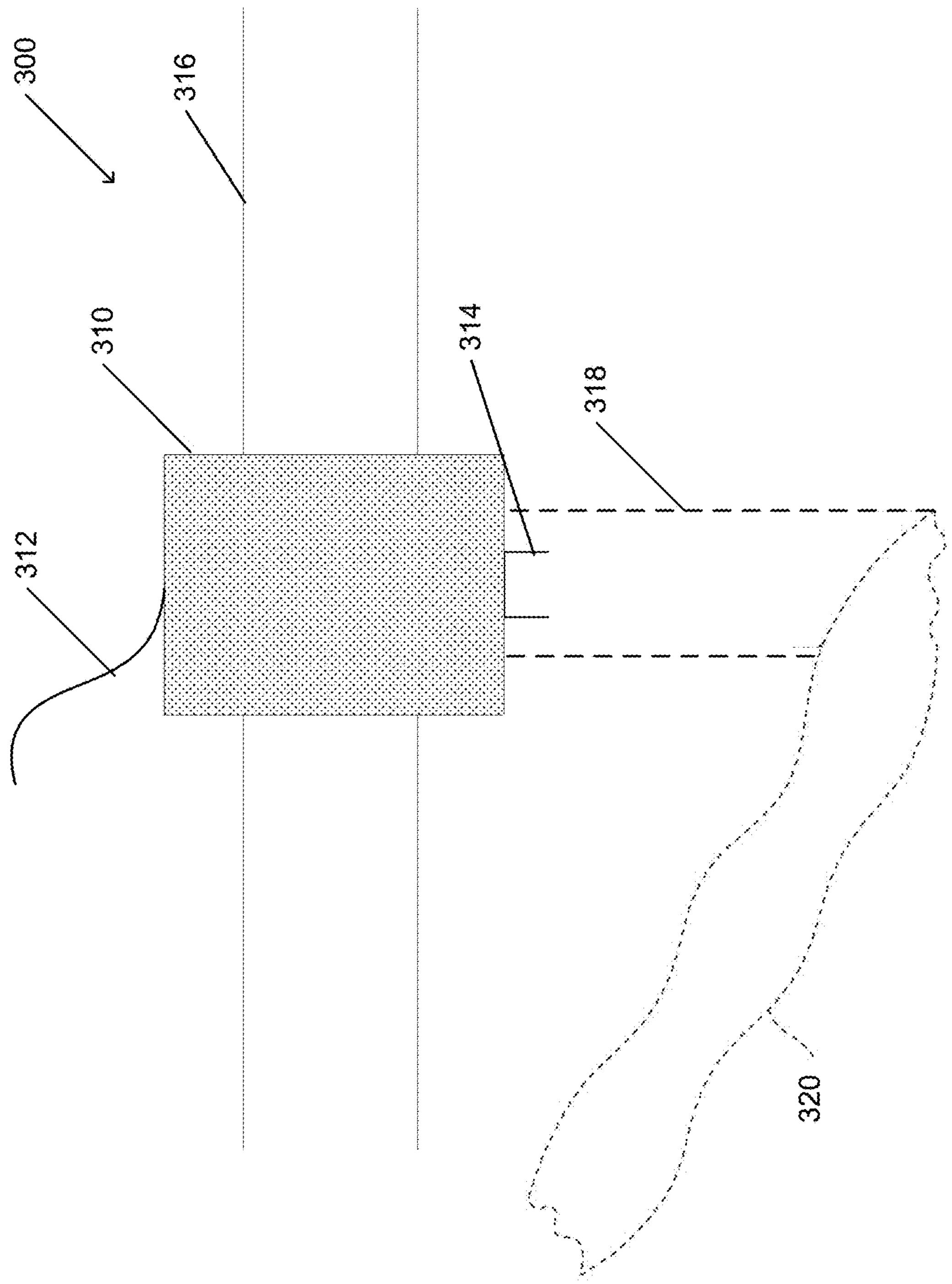
FIG. 3A is a conceptual line drawing of a dura shield coupled to an annulus of a spinal disc in accordance with an embodiment of the invention is shown.

Turning now to FIG. 3A, a conceptual line drawing of a dura shield coupled to an annulus of a spinal disc in accordance with an embodiment of the invention is shown. Portions of a body in which the dura shield may be attached are shown in dotted lines. The operating environment 300 includes a dura shield having a shield 310, tether 312, and anchor 314. The shield is deployed on dura 316 and the anchor 314 is coupled to an attachment surface 318. The attachment surface 318 is preferably an annulus of a spinal disc, but can be a spinal disc and/or any other surface within the body as appropriate to specific applications of the invention. Also shown is exiting nerve root 320. The shield 310 is opened and lies substantially in contact with to dura 316. In this way, the shield 310 protects the dura 316 from impact and/or abrasion. The tether 312 can be located within the shield 310, on top of the shield 310, and/or under the shield 310. In several embodiments, the tether 312 is located between the shield 310 and the dura 316. The tether 312 can be used to adjust the positioning of the shield 310 with respect to the dura 316.

Figure 3B:
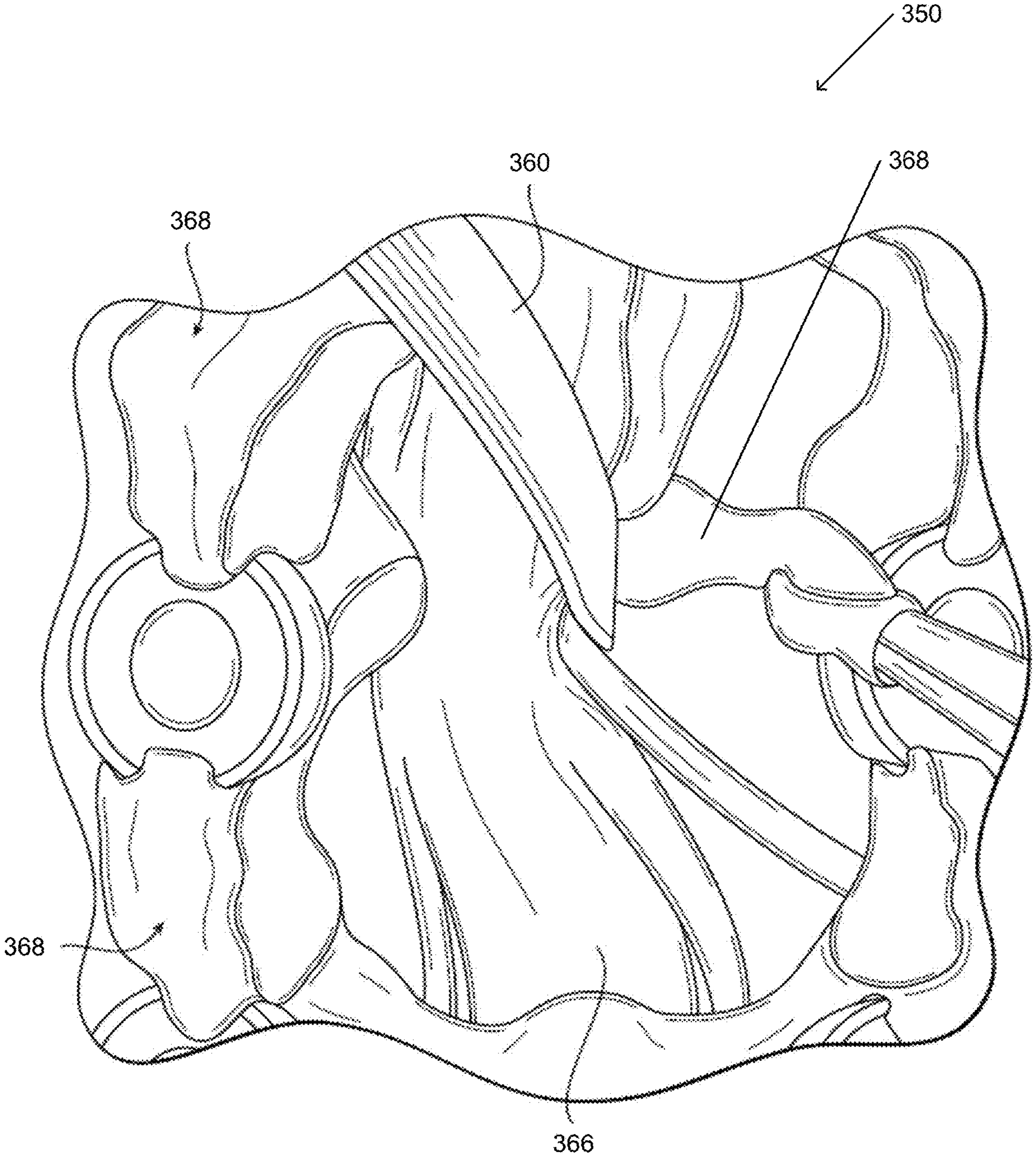
FIG. 3B is a line drawing of a dura shield in vivo in accordance with an embodiment of the invention.

Turning now to FIG. 3B, a line drawing of a dura shield in vivo in accordance with an embodiment of the invention is shown. The operating environment 350 includes a dura shield 360 deployed on dura 366 and coupled to an attachment surface. A variety of attachment surfaces 368 are shown, including an annulus of a spinal disc and a spinal disc. However, any other surface within the body can be used as an attachment surface 368 as appropriate to specific applications of the invention. The dura shield 360 is opened and lies substantially in contact with to dura 366. In operating environment 350, the dura shield 360 is being used to adjust the location of dura 366 within the operating environment 350.

Although a variety of locations and attachments of dura shields are shown and described with respect to FIGS. 3A-B, it should be noted that any other positioning and/or attachment of a dura shield within an operating environment can be used in accordance with embodiments of the invention.

Figure 4:
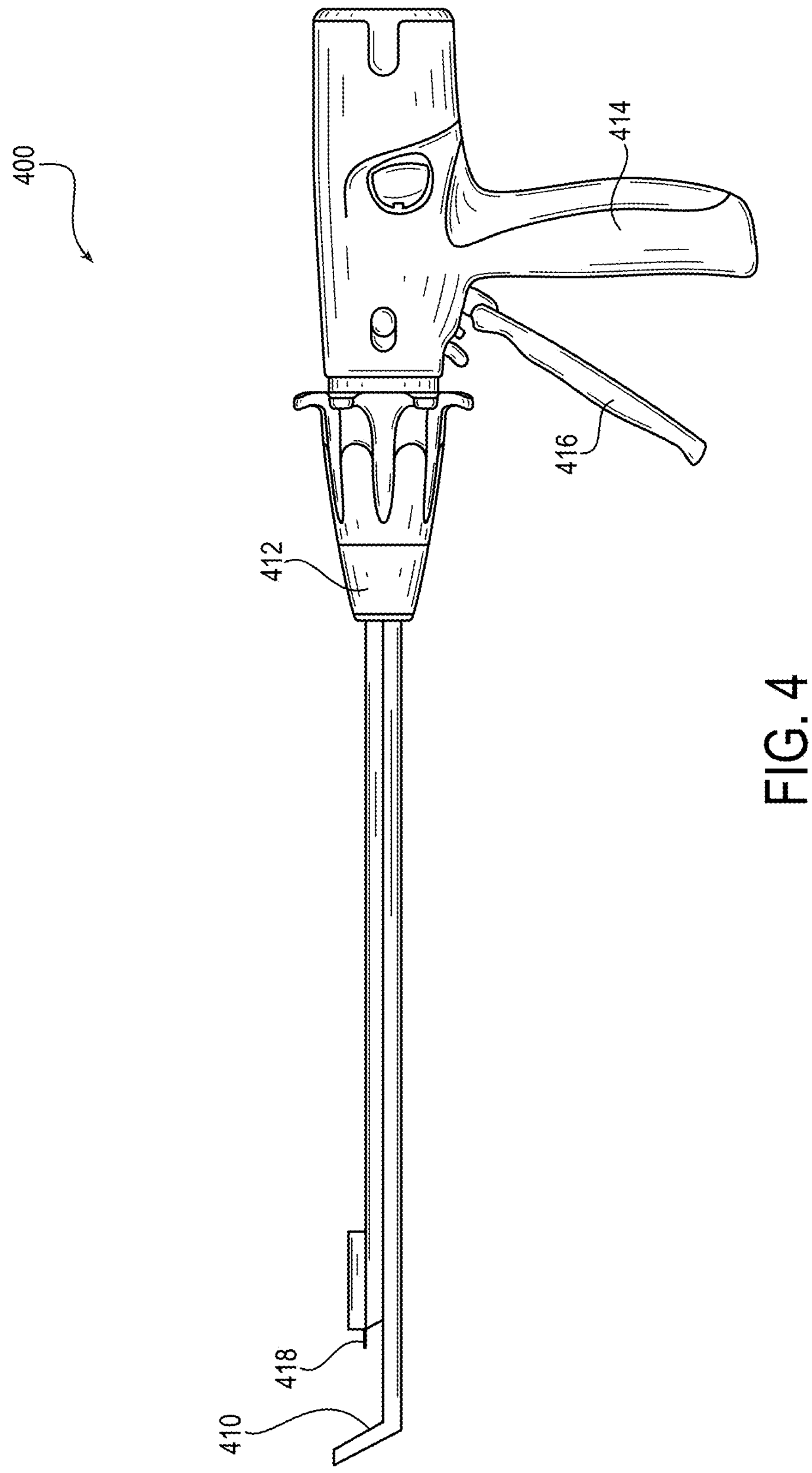
FIG. 4 is a line drawing of an applicator for a dura shield in accordance with an embodiment of the invention.

Turning now to FIG. 4, a line drawing of an applicator for a dura shield in accordance with an embodiment of the invention is shown. Internal portions of the device are shown in dotted lines. The applicator 400 includes an applicator tip 410, a body 412, a handle 414, a trigger 416, and a piston 418. As shown in FIG. 4, the applicator 400 is in an unloaded state. The applicator tip 410 and/or body 412 can be dimensioned to accept a dura shield in an unopened state. The handle 414 can be used to hold the applicator 400, and the trigger 416 can be used to push piston 418 (or other structure) holding a dura shield towards the tip 410. The applicator tip 410 can cause an anchor of a dura shield to be affixed to a surface as described herein. In several embodiments, the applicator tip 410 is angled and can be used to place a dura shield relative to an attachment surface. When the piston 418 is brought into contact (or close to) the applicator tip 410, an anchor of the dura shield can be affixed to the attachment surface. In many embodiments, piston 418 can be actuated using the trigger 416 via one or more linkages in the body 412. Once affixed, the applicator 400 can be withdrawn, leaving the affixed dura shield to the surface. The applicator tip 410, piston 418, and/or body 412 can be shaped to cause the dura shield to transition from a closed state to an open state as the applicator 400 is withdrawn. In a variety of embodiments, the geometry of the applicator tip 410 is dimensioned to manipulate the position of the dura shield as the applicator 400 is withdrawn.

Figure 5:
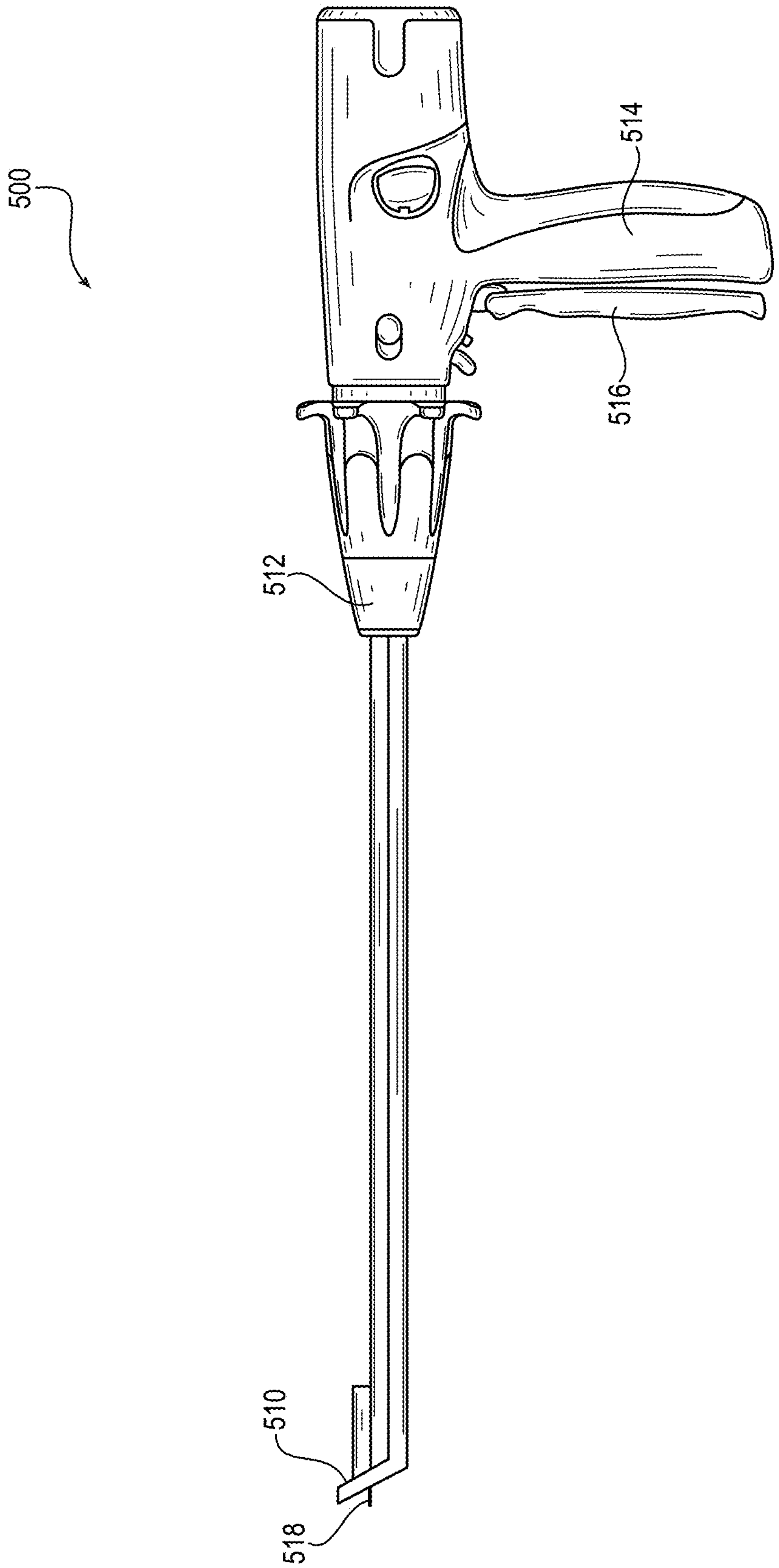
FIG. 5 is a line drawing of an applicator for a dura shield in accordance with an embodiment of the invention.

Turning now to FIG. 5, a line drawing of an applicator for a dura shield in accordance with an embodiment of the invention is shown. Internal portions of the device are shown in dotted lines. The applicator 500 includes a dura shield 518, an applicator tip 510, a body 512, a handle 514, and a trigger 516. As shown in FIG. 5, the applicator 500 is in a loaded state. The dura shield 518 can be partially and/or fully contained within the applicator tip 510 and/or body 512. In several embodiments, an anchor of the dura shield 518 is contained external to the applicator 500, while the shield and tether of the dura shield are contained within the applicator tip 510 and/or body 512. The anchor of the dura shield 518 can be placed in contact with a surface. The handle 516 can be released, causing a piston to withdrawn from the applicator tip 510 and thereby deploying the dura shield 518 as described herein. In many embodiments, the dura shield is deployed as the applicator 500 is removed from the attachment surface.

Although a variety of applicators are shown and described with respect to FIGS. 4 and 5, a variety of other applicators, including those where the trigger is located away from the handle when the applicator is in a loaded state and the trigger can be squeezed in order to deploy the dura shield, can be used in accordance with embodiments of the invention.

Although the present invention has been described in certain specific aspects, many additional modifications and variations would be apparent to those skilled in the art. In particular, any of the various processes described above can be performed in alternative sequences and/or in parallel (on the same or on different computing devices) in order to achieve similar results in a manner that is more appropriate to the requirements of a specific application. It is therefore to be understood that the present invention can be practiced otherwise than specifically described without departing from the scope and spirit of the present invention. Thus, embodiments of the present invention should be considered in all respects as illustrative and not restrictive. It can be evident to the annotator skilled in the art to freely combine several or all of the embodiments discussed here as deemed suitable for a specific application of the invention. Throughout this disclosure, terms like "advantageous," "exemplary," or "preferred" indicate elements or dimensions which are particularly suitable (but not essential) to the invention or an embodiment thereof, and can be modified wherever deemed suitable by the skilled annotator, except where expressly required. Accordingly, the scope of the invention should be determined not by the embodiments illustrated, but by the appended claims and their equivalents.

The invention claimed is:

1. A dura shield, comprising:

a shield configured to protect a patient's dura and/or nerves during an interbody procedure;

a tether extending within the shield and from a proximal end of the shield, the tether configured to position the shield; and an anchor coupled to the shield and attached to the tether, the anchor positioned distal to a distal end of the shield and configured to attach to a surface within the patient during the interbody procedure;

wherein the dura shield comprises an undeployed state where the shield is rolled around the tether and a deployed state where the shield is unrolled and the tether can be used to adjust the positioning of the shield.

2. The dura shield of claim 1, wherein the shield is constructed using a material selected from a group consisting of plastic, rubber, sponge, neoprene, polyethylene fibers, and Kevlar.

3. The dura shield of claim 2, wherein the shield comprises a first layer constructed using a first material selected from the group and a second layer constructed using a second material selected from the group, the first material differing from the second material.

4. The dura shield of claim 3, wherein the first layer provides an abrasion-resistant surface.

5. The dura shield of claim 3, wherein the second layer provides a padded surface.

6. The dura shield of claim 3, wherein the tether is located between the first layer and the second layer.

7. The dura shield of claim 1, wherein the shield comprises an antibacterial treatment.

8. The dura shield of claim 1, wherein the shield comprises a soothing treatment.

9. The dura shield of claim 1, wherein the surface is selected from the group consisting of an annulus of a spinal disc, a spinal disc, and a bone.

10. The dura shield of claim 1, wherein the anchor is selected from the group consisting of a staple, a hook, a screw, and an adhesive.

11. The dura shield of claim 1, wherein the tether is constructed from a material selected from the group consisting of a plastic, a rubber, and a metal.

12. The dura shield of claim 1, wherein the anchor is attached to the surface when the dura shield is in the deployed state.

13. The dura shield of claim 1, further comprising an applicator configured to hold the dura shield when the dura shield is in the undeployed state.

14. The dura shield of claim 13, wherein the applicator is configured to transition the dura shield from the undeployed state to the deployed state by unrolling the shield from around the tether as the applicator is withdrawn from the surface.

15. A method for attaching a dura shield, comprising:

inserting, into a piston of an applicator, a dura shield in an undeployed state, wherein an anchor of the dura shield extends beyond a first end of the piston;

placing the anchor on a surface;

actuating a trigger of the applicator to cause the piston to move toward an applicator tip of the applicator and to attach to the surface; and deploying the dura shield by withdrawing the piston from the applicator tip, wherein withdrawing the piston causes the dura shield to move from the undeployed state to a deployed state.

16. The method of claim 15, further comprising manipulating a location of the dura shield by moving a tether of the dura shield using the applicator.

17. The method of claim 15, wherein causing the anchor to attach to the surface comprises compressing a staple.

18. The method of claim 15, wherein causing the anchor to attach to the surface comprises turning a screw.

19. A dura shield system, comprising:

a dura shield, comprising:

a tether;

a shield configured to protect a patient's dura and/or nerves during an interbody procedure and coupled to the tether to adjust positioning of the shield; and an anchor coupled to the shield and configured to attach to:

an annulus of a spinal disc within the patient during the interbody procedure, or a bone of vertebral body within the patient during the interbody procedure; and an applicator configured to hold the dura shield when the shield is in an undeployed state and having a trigger actuatable to manipulate the shield from the undeployed state to a deployed state.

20. The dura shield system of claim 19, wherein the tether extends within the shield and from a proximal end of the shield, wherein the anchor is attached to the tether, the anchor positioned distal to a distal end of the shield.

* * * * *